(12) United States Patent
Patel

(10) Patent No.: US 11,958,818 B2
(45) Date of Patent: Apr. 16, 2024

(54) (R)-(2-METHYLOXIRAN-2-YL)METHYL 4-BROMOBENZENESULFONATE

(71) Applicant: Boehringer Ingelheim International GmbH, Ingelheim am Rhein (DE)

(72) Inventor: Nitinchandra D. Patel, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 129 days.

(21) Appl. No.: 17/607,429

(22) PCT Filed: Apr. 29, 2020

(86) PCT No.: PCT/US2020/030337
§ 371 (c)(1),
(2) Date: Oct. 29, 2021

(87) PCT Pub. No.: WO2020/223267
PCT Pub. Date: Nov. 5, 2020

(65) Prior Publication Data
US 2022/0213048 A1 Jul. 7, 2022

Related U.S. Application Data

(60) Provisional application No. 62/841,419, filed on May 1, 2019.

(51) Int. Cl.
| C07D 301/19 | (2006.01) |
| C07D 303/08 | (2006.01) |
| C07D 303/16 | (2006.01) |

(52) U.S. Cl.
CPC ......... *C07D 301/19* (2013.01); *C07D 303/08* (2013.01); *C07D 303/16* (2013.01)

(58) Field of Classification Search
CPC ... C07D 301/19; C07D 303/08; C07D 303/16
USPC ....................................................... 549/513
See application file for complete search history.

(56) References Cited

U.S. PATENT DOCUMENTS

| 9,181,272 | B2 | 11/2015 | Balestra et al. |
| 9,334,285 | B2 | 5/2016 | Burke et al. |
| 9,745,289 | B2 | 8/2017 | Hornberger |
| 2010/0292225 | A1 | 11/2010 | Chamoin et al. |
| 2011/0112067 | A1 | 5/2011 | Hartmann et al. |
| 2011/0118241 | A1 | 5/2011 | Hartmann |
| 2011/0172217 | A1 | 7/2011 | Fujioka et al. |
| 2013/0143863 | A1 | 6/2013 | Aebi et al. |
| 2014/0206886 | A1 | 7/2014 | Scheidt et al. |
| 2014/0323468 | A1 | 10/2014 | Balestra et al. |
| 2016/0024105 | A1 | 1/2016 | Burke et al. |
| 2016/0229807 | A1 | 8/2016 | Aebi |

FOREIGN PATENT DOCUMENTS

| CA | 2761859 | A1 | 11/2010 |
| EP | 0666256 | A1 | 8/1995 |
| EP | 2341052 | A1 | 7/2011 |
| JP | 2007297305 | A | * 11/2007 |
| JP | 2012526774 | A | 11/2012 |
| WO | 0198273 | A1 | 12/2001 |
| WO | 2007100295 | A1 | 9/2007 |
| WO | 2007116099 | A1 | 10/2007 |
| WO | 2007117982 | A2 | 10/2007 |
| WO | 2008027284 | | 4/2008 |
| WO | 2009135651 | | 11/2009 |
| WO | 2009135651 | A1 | 11/2009 |
| WO | 2010042477 | A1 | 4/2010 |
| WO | 2014055595 | | 4/2010 |
| WO | 2010107765 | A1 | 9/2010 |
| WO | 2010129467 | | 11/2010 |
| WO | 2013037779 | | 3/2013 |
| WO | 2013041591 | | 3/2013 |
| WO | 2013156423 | | 10/2013 |
| WO | 2014055595 | A1 | 4/2014 |
| WO | 2014130608 | A1 | 8/2014 |
| WO | 2014179186 | A1 | 11/2014 |
| WO | 2015101958 | A2 | 7/2015 |
| WO | 2016014736 | A1 | 1/2016 |

OTHER PUBLICATIONS

Shen et al , Synthesis of 2-(phenoxymethyl)oxirane derivatives through unexpected rearrangement of oxiran-2-ylmethyl benzenesulfonates ,2017, vol. 47, No. 4, 273-278. (Year: 2017).*
International Search Report for PCTUS2020030337 dated Aug. 10, 2020.
Abstract for JP2007297305 cited herein.
International Search Report, dated Feb. 16, 2016, PCT/ISA220, for PCT/US2015055421.
Lucas, J. Med. Chem., vol. 51, "In Vivo Active aldosterone synthase inhibitors with improved selectivity: Lead optimization providing a series of Pyridine substituted 3,4 Dihydro-1H quinolin-2-one derivatives", 2008.
Anderson, Aldosterone Synthase Inhibition in Hypertenstion, Curr. Hypertens Rep., 2013, 15, p. 484-488.
Hu, Aldosterone Synthase Inhibitors as Promising Treatments for Mineralocorticoid Dependent Cardiovascualr and renal Diseases, J. Med Chem, 2014, 57, p. 5011-5022.
Banki, Aldosterone Antagonists in Monotherapy are Protective against Streptozotocin-Induced Diabetic Nephropathy in Rats, PLOS plus One, 2012, 7, e39938.

(Continued)

*Primary Examiner* — Taylor V Oh
(74) *Attorney, Agent, or Firm* — David L. Kershner

(57) ABSTRACT

The present invention relates to compound of formula (I), wherein $R^1$ is chloro, bromo iodo or a brosylate group. The present invention also relates to methods of making this compound and its use in carrying out organic transformations.

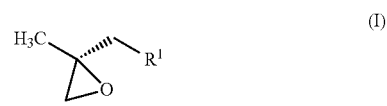

(I)

11 Claims, No Drawings

(56) References Cited

OTHER PUBLICATIONS

Dorrance, Interfering with mineralcortocid receptor activation: the past, present and future, Prime Reports, 2014, p. 6-61.
Hargovan, Aldoesterone Synthase Inhibitors in hypertension: current status and future possibilities, Journal of the Royal Society of Medicine, 2014, 0, p. 1-9.
Heim, Overcominh undesirable CYP1A2 Inhibition of Pyridylnaphthaline-Type Aldoesterone Synthase Inhibtiors: Influence of Heteroaryl Derivatization on Potency and Selectivity Journal of Medicinal Chem, 2008, 501, p. 5011-5022.
Azzizi, Nephrol Dial Transplant 2013, 28, p. 36-43.
International Report on Patetability for PCT/US2017038440 dated Jan. 10, 2019.
Sonegawa, Regioselective Alkylation of 2-Alkyl-5.6.7.8-tetrahydro-3H-cycloheptimidazol-4ones and 2-Alkyl-3H-cycloheptimidazol-4-ones, Chem and pharm Bulletin, 2006, vol. 54, p. 706-710.
Mityanov, Regioselective synthesis of 2-unsubstituted 1-aryl-4-and 1-aryl-5 acylimiazoles Tetrahedron, 2014, vol. 70, p. 3545-3552.
Bornstein, Phase 1C study of the aldosterone synthase inhibitor BI 690517 in diabetic patients with kidney disease, Journal of the American Society of Nephrology, vol. 32, 2021, p. 264-265.
International Search Report, PCT/ISA/210, dated Aug. 8, 2014, for PCT/US2014/035596.
International Search Report and Written Opinion, PCT, US 2015/041648, PCT/ISA/220, dated Oct. 26, 2015.
Hartmann, et al, "Discovery of selective CYP11B2 (aldosterone synthase) inhibitors for the therapy of congestive heart failure and myocardial fibrosis", Euro. Journal of Medicinal Chamistry, vol. 38, No. 4, 2003.
International Search Report and Written Opinion, Form ISA220, dated Feb. 22, 2016, for PCT/US2015063064.
International Preliminary Report on Patentability, Form PCT.IB/373, dated Jun. 6, 2017.
Martin, Synthesis of annulated pyridines as inhibitors of aldosterone synthase, Organic Biomol. Chemistry, vol. 14, 2016, 2016.
Azizi, Aldosterone synthase inhibitors in humans, Nephrol Dial Translplant, vol. 28, p. 36-43. 2012.
Hu, Aldosterone Synthase Inhibitors as promising treatments for mineralocorticoid dependent cardiovascular and renal diseases, Phamraceutical and Medicinal chem, vol. 57, 2014, p. 5011-5022.
Banki, Aldosterone Antagonists in Monotherapy are protective against Streptozotocin-induced diabetic Neuropathy in rats, PLoS One, vol. 7, e39938, 2012.
Andersen, Aldosterone Synthase Inhibitors in Hypertension, Current Hypertens Rep., vol. 15, 2013, p. 484-488.
Hargovan, Aldosterone synthase inhibitors in hypertension: current status and future possibilities, Journal of the Royal Society of Medicine Cardiovascular Disease, 2014, p. 1-9.
Dorrance, Interfering with mineralcorticoid receptor activation: the past, present and future, F1000 Prime Reports, 2014, p. 6-61.

\* cited by examiner

(R)-(2-METHYLOXIRAN-2-YL)METHYL 4-BROMOBENZENESULFONATE

FIELD OF THE INVENTION

The present invention relates to (R)-(2-methyloxiran-2-yl)methyl-4-bromobenzenesulfonate and its halo analogs, methods for making these compounds, and their use in carrying out organic transformations.

BACKGROUND

The compound (R)-(2-methyloxiran-2-yl)methyl-4-nitrobenzenesulfonate (A) has the structure shown below and is useful as a starting material or intermediate for preparation of more complex chemical compounds as described, for example, in US2018162878, WO 2005/037814, and EP 1553088.

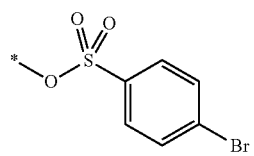 [SMILES: *OS(=O)(=O)c1ccc(Br)cc1]

However, Compound A is highly energetic and reactions involving this compound require special handling and processing equipment. Therefore, there is a need for less-energetic alternatives to Compound A for carrying out organic transformations.

BRIEF SUMMARY OF THE INVENTION

In a first aspect (embodiment 1), the invention relates to a compound of formula I:

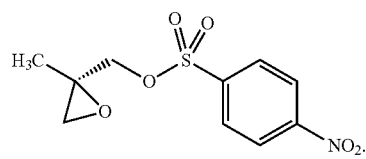

wherein $R^1$ is chloro, bromo iodo or a brosylate group having the structure:

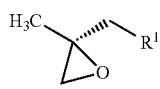

wherein the asterisk (*) denotes the point of attachment.

The compound of formula I can be used as a starting material and intermediate for asymmetric organic transformations, for example, those organic transformations that might otherwise utilize the highly energetic Compound A. Organic transformations involving the compound of formula I are less exothermic than similar organic transformations involving Compound A. Thus, the compound of formula I is a safer alternative to Compound A for carrying out organic transformations and is more amenable to use in large-scale (commercial) processes.

In another embodiment (embodiment 2), the invention relates to the compound of formula I, wherein $R^1$ is a brosylate (hereinafter "Compound 1") and having the structure:

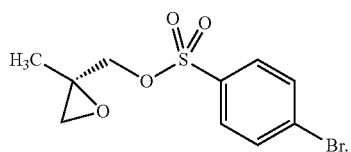

In another embodiment, (embodiment 3), the invention relates to the compound of formula I, wherein X is iodo (hereinafter "Compound 2") and having the structure:

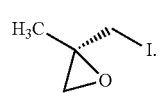

Other embodiments of the invention relate to methods of making the compounds of formula I and their use in organic transformations.

Water Scavenger Process

In one embodiment, (embodiment 4), the process of the invention relates to a process for making Compound 1, comprising:
  (i) contacting an admixture comprising methylallyl alcohol, (+)-di-isopropyl L-tartrate (L-DIPT) and a solvent/diluent with molecular sieves to provide a first anhydrous admixture;
  (ii) cooling the first anhydrous admixture;
  (iii) adding Ti(O-iPr)$_4$ to the cooled anhydrous admixture in step (ii) to provide a second anhydrous admixture;
  (iv) adding cumene hydroperoxide to the second anhydrous admixture of step (iii) to provide a first reaction mixture;
  (v) allowing the contents of the first reaction mixture to react to provide an admixture comprising INT-1;

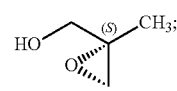

(vi) filtering the admixture obtained from step (v) to provide a filtrate comprising INT-1;
  (vii) optionally treating the filtrate obtained from step (vi) with trimethylphosphite to quench unreacted cumene hydroperoxide ("the quenched filtrate"); and
  (viii) treating the filtrate from step (vi) or the optionally quenched filtrate of step (vii) with triethylamine (Et$_3$N), 4-dimethylaminopyridine (DMAP), and 4-bromobenzene-1-sulfonyl chloride (BrsCl) to provide a second reaction mixture; and
  (ix) allowing the contents of the second reaction mixture to react to provide an admixture comprising Compound 1.

Embodiments of the inventions that comprise a water scavenger such as embodiment 4 are also referred to herein as "water scavenger processes."

In another embodiment (embodiment 5), the molecular sieves used in step (i) of the water scavenger process is 4 Å molecular sieves.

In another embodiment (embodiment 6), the solvent/diluent used in step (i) of the water scavenger process is methylene chloride or toluene.

In another embodiment (embodiment 7), the solvent/diluent used in step (i) of the water scavenger process is methylene chloride or toluene.

In another embodiment (embodiment 8), the invention relates to any of embodiments 4 to 7, further comprising:
(x) isolating Compound 1 from the admixture of step (ix).

In another embodiment (embodiment 9), the invention relates to a process for making Compound 1, comprising:
(i) contacting an admixture comprising methylallyl alcohol, (+)-di-isopropyl L-tartrate (L-DIPT) and a solvent/diluent with 4 Å molecular sieves to provide a first anhydrous admixture;
(ii) cooling the first anhydrous admixture;
(iii) adding Ti(O-iPr)₄ to the cooled first anhydrous admixture in step (ii) to provide a second anhydrous admixture;
(iv) adding cumene hydroperoxide to the second anhydrous admixture of step (iii) to provide a first reaction mixture;
(v) allowing the contents of the first reaction mixture to react to provide an admixture comprising INT-1;

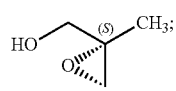

INT-1

(vi) filtering the admixture obtained from step (v) to provide a filtrate comprising INT-1;
(vii) treating the filtrate obtained from step (vi) with trimethylphosphite to quench unreacted cumene hydroperoxide ("the quenched filtrate"); and
(viii) treating the quenched filtrate of step (vii) with triethylamine (Et₃N), 4-dimethylaminopyridine (DMAP), and 4-bromobenzene-1-sulfonyl chloride (BrsCl) to provide a second reaction mixture;
(ix) allowing the contents of the second reaction mixture to react to provide an admixture comprising Compound 1; and
(x) isolating Compound 1 from the admixture of step (ix).

Azeotropic Distillation Process

In yet another embodiment (embodiment 10), the process of the invention relates to a method for making Compound 1, comprising:
(i) carrying out an azeotropic distillation of solution comprising cumene hydroperoxide and a solvent capable of forming an azeotrope to provide a first anhydrous solution;
(ii) cooling the first anhydrous solution;
(iii) carrying out an azeotropic distillation of a solution comprising methylallyl alcohol, (+)-di-isopropyl L-tartrate (L-DIPT), and a solvent capable of forming an azeotrope to provide a second anhydrous solution;
(iv) cooling the second anhydrous solution;
(v) adding titanium tetraisoproxide (Ti(O-iPr)₄) to the cooled second anhydrous solution in step (iv);
(vi) combining the cooled first solution from step (ii) with the cooled second anhydrous solution from step (v) to provide a first reaction solution;

(vii) allowing the contents of the first reaction solution from step (vi) to react to provide a solution comprising INT-1;
(viii) optionally treating the solution obtained from step (vii) with trimethylphosphite to quench unreacted cumene hydroperoxide; and
(ix) treating the solution obtained from step (vii), or the optionally quenched solution of step (viii), with triethylamine (Et₃N), 4-dimethylaminopyridine (DMAP), and 4-bromobenzene-1-sulfonyl chloride (BrsCl) to provide a reaction solution comprising Compound 1.

Embodiments of the invention that comprise an azeotropic distillation such as embodiment 10 are also referred to herein "azeotropic distillation processes."

In another embodiment (embodiment 11), the solvent capable of forming an azeotrope used in step (i) and step (iii) of the azeotropic distillation process is methylene chloride or toluene.

In another embodiment (embodiment 12), the invention relates to embodiment 10 or 11, further comprising:
(x) isolating Compound 1 from the reaction solution of step (ix).

In another embodiment (embodiment 13), the process of the invention relates to a method for making Compound 1, comprising:
(i) carrying out an azeotropic distillation of solution comprising cumene hydroperoxide and methylene chloride to provide a first anhydrous solution;
(ii) cooling the first anhydrous solution;
(iii) carrying out an azeotropic distillation of a solution comprising methylallyl alcohol, (+)-di-isopropyl L-tartrate (L-DIPT), and methylene chloride to provide a second anhydrous solution;
(iv) cooling the second anhydrous solution;
(v) adding titanium tetraisoproxide (Ti(O-iPr)₄) to the cooled second anhydrous solution in step (iv);
(vi) combining the cooled first anhydrous solution from step (ii) with the cooled second anhydrous solution from step (v) to provide a first reaction solution;
(vii) allowing the contents of the first reaction solution from step (vi) to react to provide a solution comprising INT-1;
(viii) optionally treating the solution obtained from step (vii) with trimethylphosphite to quench unreacted cumene hydroperoxide;
(ix) treating the solution obtained from step (vii), or the optionally quenched solution of step (viii), with triethylamine (Et₃N), 4-dimethylaminopyridine (DMAP), and 4-bromobenzene-1-sulfonyl chloride (BrsCl) to a provide an admixture comprising Compound 1; and
(x) isolating Compound 1 from the admixture of step (ix).

In another embodiment (embodiment 14), the process of the invention relates to a method for making the compound of formula I wherein R¹ is chloro, bromo or iodo, comprising:
reacting Compound 1 with a tetraethylammonium halide (TEAX) to provide the compound of formula I wherein X (halide) is chloride, bromide or iodide

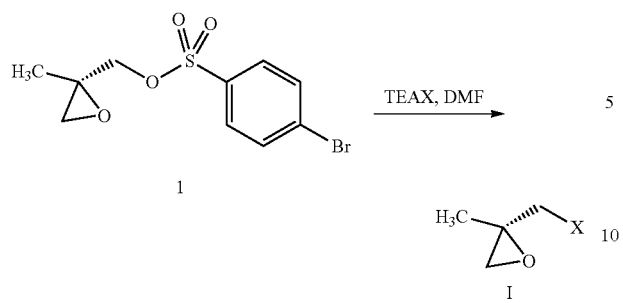

wherein X is chloride, bromide or iodide.

In another embodiment (embodiment 15), the invention relates to the process of embodiment 14, wherein X is I (iodo).

Additional embodiments of the invention are described in the Detailed Description of the Invention and Examples below.

DETAILED DESCRIPTION OF THE INVENTION

Abbreviations

BrsCl 4-Bromobenzene-1-sulfonyl chloride
CHP Cumene hydroperoxide
$CH_2Cl_2$ Dichloromethane, methylene chloride
DMAP 4-Dimethylaminopyridine
DMF Dimethylformamide
e.e. Enantiomeric excess
$Et_3N$ Triethylamine
EtOAc Ethyl acetate
GC Gas chromatography
HPLC High performance liquid chromatography
$NH_4Cl$ Ammonium chloride
L-DIPT Di-isopropyl L-tartrate
$P(OMe)_3$ Trimethylphosphite
$R_f$ Retention factor
RT Room temperature
TEAI Tetraethylammonium iodide
tert-BuOK Potassium tertiary-butoxide
$Ti(O\text{-}iPr)_4$ Titanium(IV) (isopropoxide)

As described above, the invention relates to compounds of formula I and processes for making and using such compounds. The invention arises out of a need for a safer, less energetic alternative to processes using Compound A. Applicant found that could be used a replacement for organic transformations using compound A. Advantageously, reactions involving compounds of formula I are less exothermic than reactions involving Compound A. Thus, organic transformations using Compound 1 are more amenable to commercial-scale processes.

Methods of making Compound A generally require use of molecular sieves to scavenge water that may be present during the epoxidation step. See, e.g., WO 2005/037814 A1, EP 1553088 A1, and US2018162878. The use of molecular sieves as a water scavenger can be used to prepare Compound 1 referred to herein as the water scavenging process. The process is depicted in Scheme 1.

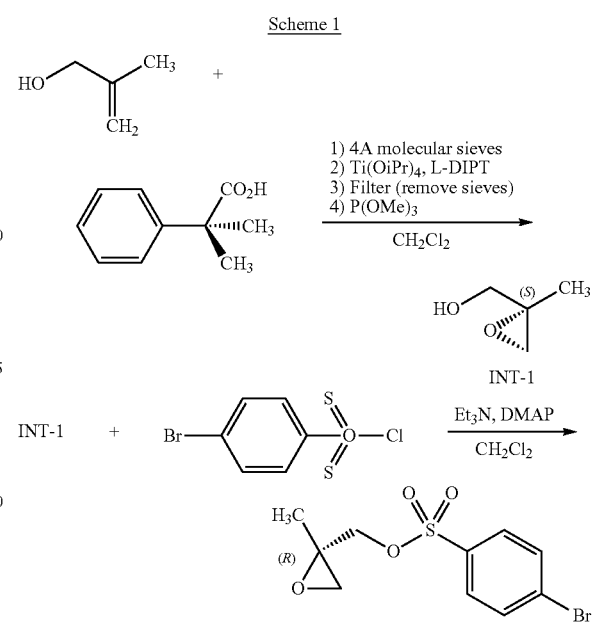

Scheme 1

As depicted in Scheme 1, methylallyl alcohol (1 molar equivalent) is reacted with excess cumene hydroperoxide (about 1.9 molar equivalent) in dichloromethane diluent under anhydrous conditions and at reduced temperature, e.g., between −15° C. to 0° C. to form INT-1 and water (not shown). As shown in Scheme 1, the reaction is carried out in the presence of a catalyst (about 0.06 molar equivalent) formed in situ from titanium (IV) isopropoxide and (+)-diisopropyl L-tartrate. This catalyst will react with water that may be present in the reaction mixture, rendering the catalyst inactive. Therefore, the reaction to form INT-1 is also carried out in the presence of a sufficient quantity of 4 Å molecular sieves to maintain a low water content during the reaction process, e.g., less than 100 ppm, or 60 about ppm in the liquid diluent. The reaction is carried out for sufficient time and at sufficient temperature to form INT-1. The reaction mixture is then filtered through Celite® to remove molecular sieves. The filtrate containing INT-1 is cooled (e.g., −15° C. to −5° C.) and treated with trimethylphosphite (about 1 molar equivalent) to quench unreacted cumene hydroperoxide. The cooled (quenched) filtrate is then treated with 4-bromobenzene-1-sulfonyl chloride (1 molar equivalent), trimethylamine (about 1.2 molar equivalents), and 4-dimethylaminopyridine (about 0.059 molar equivalents) and stirred for a sufficient time (e.g., 6 hours) and at a sufficient temperature (e.g., −5° C.) to allow substantially all the 4-bromobenzene-1-sulfonyl chloride to react to provide Compound 1. Compound 1 can then be isolated from the reaction mixture using procedures described in the Examples section or known to those skilled in the art.

An alternative method for making Compound 1 (described herein as the azeotropic distillation process) does not require molecular sieves and advantageously avoids the filtration step discussed above in the molecular sieve scavenger process. Instead of relying on a water scavenger, Applicant found that water evolved or present during formation of INT-1 can be removed via azeotropic distillation. A nonlimiting embodiment for making Compound 1 according to the azeotropic distillation process is depicted in Scheme 2.

Scheme 2.

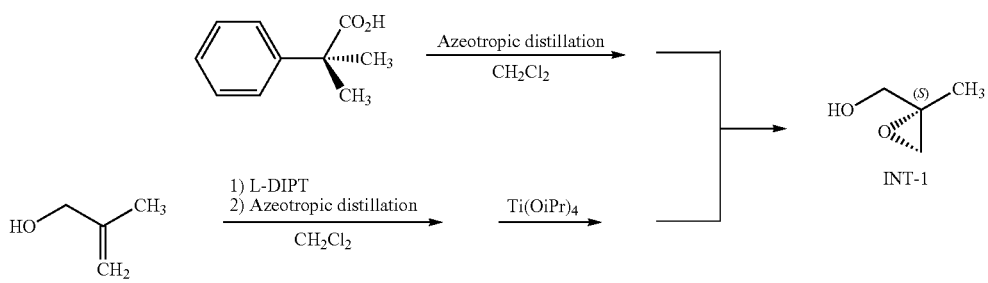

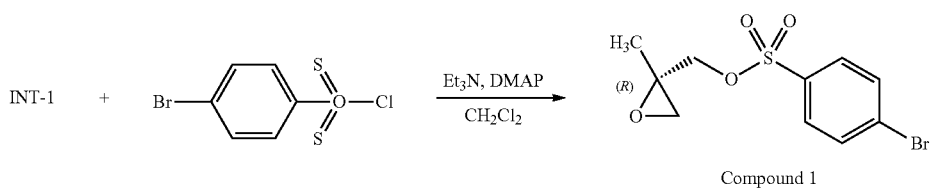

As depicted in Scheme 2, a solution of methylallyl alcohol (1 molar equivalent), (+)-diisopropyl L-tartrate (0.06 molar equivalents) in dichloromethane is distilled to remove water until the water content is less than 60 ppm. The reactor contents are then cooled to 0 to ~15° C. and treated with Ti(OiPr)$_4$ (0.05 molar equivalents). In a separate reactor, a solution of CHP (1.1 molar equivalents) in dichloromethane is distilled to remove water through azeotropic distillation of dichloromethane. The CHP solution is then cooled to −15° C. and slowly added to the reactor containing the methylallyl alcohol. The reaction is allowed to proceed for a sufficient time (e.g., 24 hours) and at a sufficient temperature (e.g., −15° to −5° ° C.) to allow substantially all the methylallyl alcohol to react. The reactor contents are cooled (e.g., −15° C.) and treated with trimethylphosphite (0.45 molar equivalents) to quench unreacted cumene hydroperoxide. The quenched solution is further treated at reduced temperature (−15° C. to −5° C.) with triethylamine (1.1 molar equivalents), 4-dimethylaminopyridine (0.05 molar equivalent) and 4-bromobenzene-1-sulfonyl chloride (0.95 molar equivalents) and stirred for a sufficient time (e.g., 2-6 hours) and at a sufficient temperature (e.g., −5° C.) to allow substantially all the 4-bromobenzene-1-sulfonyl chloride to react to provide Compound 1. Compound 1 can then be isolated from the reaction mixture using procedures described in the Examples section or known to those skilled in the art. In one embodiment, Compound 1 is crystallized from n-butanol and heptane.

Methods of Using Compound 1

The invention also relates to methods for using Compound 1 as a reagent for organic transformations. Nonlimiting examples include those where Compound 1 is used as a replacement/alternative for Compound A, for example, as described in US2018162878, WO 2005/037814, and EP 1553088.

A non-limiting method for using Compound 1 to carry out an organic transformation is depicted below in Scheme 3 for preparing Compound 2.

Scheme 3.

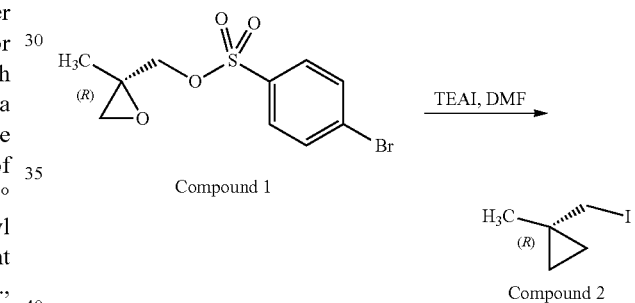

wherein TEAI is tetraethylammonium iodide.

EXAMPLES

Example 1

Preparation of Compound 1 (Method A)

Molecular sieves (4 Å) powder (40.0 g) are charged to a multi-neck 1 L jacketed reactor equipped with a mechanical stirrer, thermocouple and a nitrogen inlet. The reactor is evacuated and refilled three times with nitrogen. Dichloromethane (400 mL) is charged to the reactor followed by methylallyl alcohol (40.0 g, 555.0 mmol) and (+)-diisopropyl L-tartrate (6.955 mL, 33.28 mmol, 6.0 mol %). The resulting mixture is cooled to −15° C., treated with titanium (IV) isopropoxide (8.21 mL, 28.0 mmol, 5.0 mol %) at −15° C., and stirred for additional 0.5 h. 90% Technical cumene hydroperoxide (194.6. 1054.0 mmol, 1.9 equiv.) is charged to the reactor dropwise at −15° C. to −5° C. and agitated at 0° C. for 24 h. The reaction mixture is filtered through a short pad of Celite®, and trimethylphosphite (65.4 mL, 555.0 mmol, 1.0 equiv.) is added dropwise to the filtrate at −15° C. to −5° C. to quench excess cumene hydroperoxide. The quenched filtrate reactor is treated with triethylamine (92.79 mL, 666.0 mmol, 1.2 equiv.), 4-dimethylaminopyridine (4.06 g, 33.0 mmol, 6.0 mol %) followed by dropwise addition of a solution of 4-bromobenzene-1-sulfonyl chloride (141.75 g, 555.0 mmol, 1.0 equiv.) in dichloromethane (320 mL) at −15° C. to −5° C. The reactor contents are maintained at −5° C. for additional 6 h after which HPLC analysis indicates >97% conversion. The reaction mixture is washed with an aqueous solution of 13% tartaric acid (460 g, 400.0 mmol, 0.72 equiv.), an aqueous solution of 7% sodium bicarbonate (431.0 g, 369.0 mmol, 0.66 equiv.), and then with an aqueous solution of saturated brine (270.0 g, 1198.0 mmol, 2.15 equiv.) in this order. The resulting organic layer is dried over magnesium sulfate (20 g) and concentrated under reduced pressure to obtain crude product as a brown oil (375.0 g). The crude product is purified by silica gel pad filtration (335 g) by eluting with 20% to 50% EtOAc in hexanes. The combined product fractions are combined and concentrated under a reduced pressure to afford 327 g of clear oil to which hexanes (150 mL) is added. The resulting mixture is transferred into a 500 mL multi-neck jacketed reactor, cooled to −2° C., and stirred for 20 h at 0° C. to afford a white slurry. The solids are collected by filtration, rinsed with hexanes (50 mL) followed by vacuum drying at ambient temperature with a nitrogen stream to afford Compound 1 as white solids (Yield: 78.0 g, 46.0%) with HPLC area purity>99%. Optical purity: 96.0% e.e. (enantiomeric excess) (Chirapak AD-3, 94% heptane & 6% IPA). $^1$HNMR (CDCl$_3$, 400 MHz): δ 7.79-7.77 (m, 2H), 7.72-7.69 (m, 2H), 4.12 (d, J=10.8 Hz, 1H), 3.96 (d, J=10.8 Hz, 1H), 2.70 (d, J=4.4 Hz, 1H), 2.66 (d, J=4.4 Hz, 1H), 1.37 (s, 3H); $^{13}$CNMR (CDCl$_3$, 100 MHz): δ 134.8, 132.7, 129.4, 129.3, 73.5, 54.2, 51.7, 17.9.

Example 2

Preparation of Compound 1 (Method B)

Reactor 1: To a 3-neck 2 L jacketed reactor 1 (Reactor 1) equipped with a thermocouple, mechanical stirring, condenser and a nitrogen inlet is charged 80% tech. grade solution of cumene hydroperoxide (CHP) (211.8. 1.11 mol, 1.1 equiv.) followed by dichloromethane (1741 g). The jacket temperature is increased to 35° C. and dichloromethane is distilled under reduced pressure while keeping the internal temperature between 15° C. to 25° C. to adjust batch volume to about 530 mL. Additional dichloromethane (1306 g) is charged to reactor 1 and distillation is continued with above conditions down to a batch volume of about 530 mL.

Reactor (2): A separate reactor (Reactor 2) (with similar size and set up as Reactor 1) is charged with methylallyl alcohol (72.44 g, 1.0 mol), (+)-diisopropyl L-tartrate (14.44 g, 0.06 mol, 6.0 mol %) and dichloromethane (1742 g). The jacket temperature is increased to 35° C., and dichloromethane is distilled under reduced pressure while keeping the internal temperature between 15° C. and 25° C. to adjust batch volume to about 430 mL. Additional dichloromethane (1306 g) is charged to the reactor and the distillation is continued with the above conditions down to batch volume of about 430 mL and to bring the water content of the mixture below 60 ppm (as checked by Karl Fischer titration). The reactor contents are cooled to between 2° C. to −15° C. and charged with titanium (IV) isopropoxide (12.92 g, 0.05 mol, 5.0 mol %) while keeping the temperature below −5° C. The resulting mixture is stirred for an additional 15 min. and cooled to 15° C.

The CHP solution from Reactor 1 is cooled (−15° C.) and slowly added to Reactor 2 while keeping the internal temperature below −5° C. The reaction mixture is stirred for additional 18 h after which the GC analysis indicates conversion>93% to epoxide alcohol ((S)-(2-methyloxiran-2-yl) methanol) (INT-1).

The reaction mixture containing INT-1 is cooled to −15° C. and treated drop-wise with trimethylphosphite (55.83 g, 0.45 mol, 0.45 equiv.) at −15° C. to −5° C. to quench excess CHP. Triethylamine (111.6 g, 1.1 mol, 1.1 equiv.) and 4-dimethylaminopyridine (6.58 g, 0.05 mol, 6.0 mol %) are charged to the quenched mixture. The contents of the reactor are maintained at a temperature from −15° C. to −5° C. and treated dropwise with 4-bromobenzene-1-sulfonyl chloride (238.0 g, 0.91 mol, 0.91 equiv.) in dichloromethane (695 g). The contents of the reactor are stirred at −5° C. for 2-6 h until HPLC analysis indicates consumption of 4-bromobenzene-1-sulfonyl chloride to >99%. The reaction mixture is washed with an aqueous solution of 13% tartaric acid (754 g, 0.66 mol, 0.65 equiv.), an aqueous solution of 7% sodium bicarbonate (706 g, 0.6 mol, 0.6 equiv.) and then with an aqueous solution of saturated brine (371 g, 0.63 mol, 0.63 equiv.) in this order. The resulting dichloromethane layer is distilled under a reduced pressure while maintaining an internal temperature between 20° C. to 25° C. for the initial part of the distillation and slowly increased to 30° C. under increasing vacuum to provide an orange-colored oil (510.0 g). Heptane (181 g) is added to the crude oil is and the distillation is continued under reduced pressure while keeping the internal temperature below 25° C. to provide a dark brown oil which is polish-filtered and transferred to a clean 2 L reactor (Reactor 3).

Reactor 3. To a third reactor (Reactor 3) is charged the dark brown oil from immediately above, n-butanol (389 g), and heptane (584 g). The contents of the reactor are cooled to 20° C. and seeded with pure seeds of Compound 1 (1-2 wt %) (obtained, for example, from Example 1), stirred at 20° C. for 3-4 h, cooled to 0° C. over 4 h, and held at 0° C. for 18 h. The solids are collected by suction filtration, and the wet cake is washed with a mixture of n-butanol (98 g) and heptane (389 g) followed by heptane (486 g). The wet solids are dried under vacuum at 20° C. to afford Compound 1 as white solids (Yield: 160 g, 51.9%) with HPLC area purity>99%. Optical purity: 98.2% e.e. (enantiomeric excess) (Chirapak AD-3, 94% heptane & 6% IPA).

Example 3

Preparation of Delamanid

Compound 1 is used to prepare delamanid, a compound useful for treating multidrug-resistant tuberculosis (MDR-TB). As depicted below, Compound 1 is reacted with 2-bromo-4-nitro-1H-imidazole to provide intermediate (S)-2-bromo-1-((2-methyloxiran-2-yl)methyl)-4-nitro-1H-imidazole. This intermediate is then used to prepare delamanid as described in EP 1553088 and depicted below.

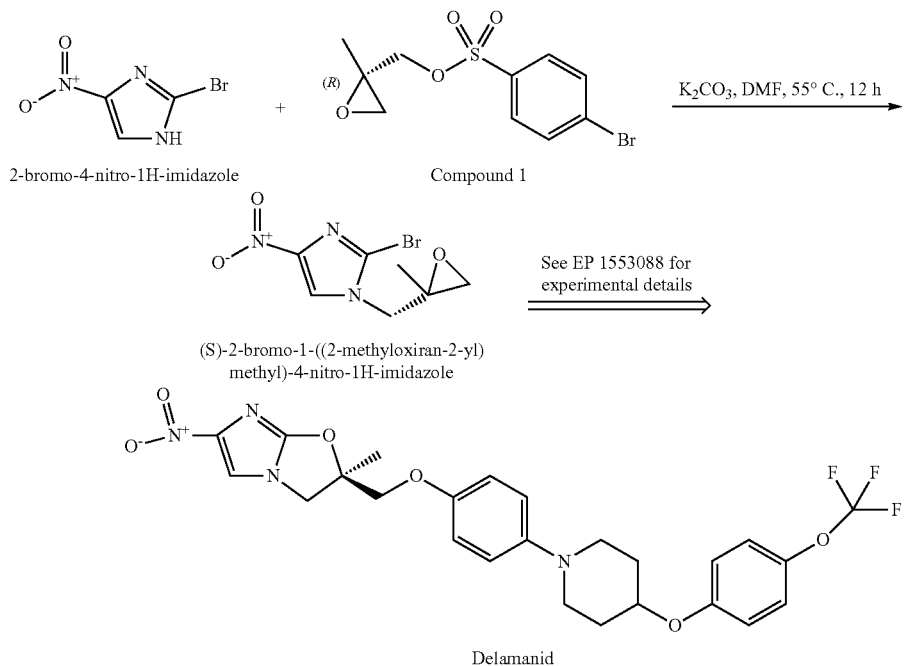

Preparation of (S)-2-bromo-1-((2-methyloxiran-2-yl)methyl)-4-nitro-1H-imidazole: 2-bromo-4-nitro-1H-imidazole (0.5 g, 2.61 mmol, 1 eq), Compound 1 (0.92 g, 2.995 mmol, 1.15 eq), $K_2CO_3$ (1.08 g, 7.81 mmol, 3.0 eq), and DMF (3.0 mL) are charged to a 50 mL round bottom flask under nitrogen and heated to 55° C. for 12 h under nitrogen. The reaction mixture is quenched with a cold solution of saturated $NH_4Cl$ (8 mL) and diluted with water (10 mL) and EtOAc (25 mL). The resulting mixture is passed through a Frit funnel to provide two layers. The top organic layer is washed with water (10 mL) and the resulting organics are dried over magnesium sulfate. The filtrate is concentrated under reduced pressure to dryness and purified using Silica gel column chromatography (0-70% EtOAc in hexanes; $R_f$ 0.67 in 100% EtOAc) to afford (S)-2-bromo-1-((2-methyloxiran-2-yl)methyl)-4-nitro-1H-imidazole in 60% yield (0.410 g, 1.57 mmol) as light yellow oil which upon cooling solidified to provide a beige solid. As noted above, the product can be used to prepare delaminid as described in EP 1553088.

Example 4

Preparation of (R)-2-(iodomethyl)-2-methyloxirane (Compound 2)

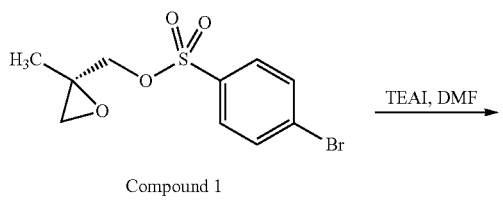

-continued

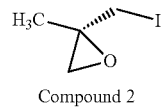

Compound 2

Tetraethylammonium iodide (TEAI) (4.6 g, 17.91 mmol, 110 mol %) and N,N-dimethylformamide (13.3 mL) are charged to a 3-neck round bottom flask equipped with a stir bar and a nitrogen line. The resulting mixture is cooled to 5° C. and charged with a solution of Compound 1 5.0 g, 16.3 mmol, 1.0 equiv.) in N,N-dimethylformamide (6.8 mL) while keeping the internal temperature below 12° C. The resulting mixture is stirred between 20° C. to 30° C. for additional 24 h after which HPLC indicates >98% conversion. The crude product (Compound 2) is used as is without further purification for the next step.

Example 5

Alternate Method for Preparation of (S)-2-bromo-1-((2-methyloxiran-2-yl)methyl)-4-nitro-1H-imidazole In a manner similar to that described in Example 3, Compound 2 can be used to prepare (S)-2-bromo-1-((2-methyloxiran-2-yl)methyl)-4-nitro-1H-imidazole.

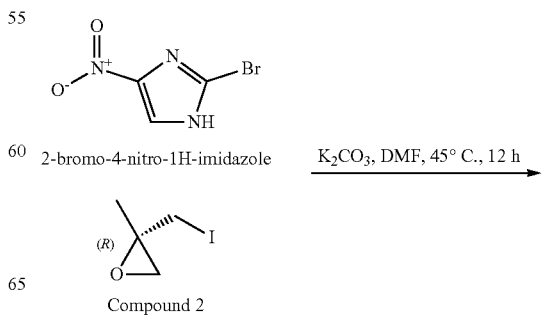

-continued

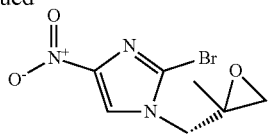

2-bromo-4-nitro-1H-imidazole (0.734 g, 3.83 mmol, 1 eq), the crude mixture of Compound 2 from Example 4 (9.7 g at 9 wt % in DMF, 4.4 mmol, 1.15 eq), $K_2CO_3$ (1.59 g, 11.5 mmol, 3.0 equiv), and DMF (4.0 mL) are charged to a 50 mL round bottom flask under nitrogen atmosphere and heated to 45° C. for 12 h. The reaction mixture is quenched with a cold solution of saturated $NH_4Cl$ (10 mL) and diluted with water (20 mL) and EtOAc (35 mL). The top organic layer is washed with water (20 mL) and the resulting organics are dried over magnesium sulfate. The filtrate is concentrated under reduced pressure to dryness and purified using Silica gel column chromatography (0-70% EtOAc in hexanes; $R_f$ 0.67 in 100% EtOAc) to afford (S)-2-bromo-1-((2-methyl-oxiran-2-yl)methyl)-4-nitro-1H-imidazole in ~70% yield (0.7 g, 2.68 mmol) as light yellow oil which upon cooling solidified to provide a beige solid. As noted above in Example 3, the product can be used to prepare delaminid as described in EP 1553088.

What is claimed is:
1. A process for making Compound 1:

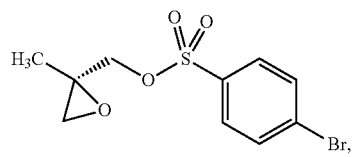

the process comprising:
(i) contacting an admixture comprising methylallyl alcohol, (+)-di-isopropyl L-tartrate (L-DIPT) and a solvent/diluent with molecular sieves to provide a first anhydrous admixture;
(ii) cooling the first anhydrous admixture;
(iii) adding $Ti(O-iPr)_4$ to the cooled anhydrous admixture in step (ii) to provide a second anhydrous admixture;
(iv) adding cumene hydroperoxide to the second anhydrous admixture of step (iii) to provide a first reaction mixture;
(v) allowing the contents of the first reaction mixture to react to provide an admixture comprising INT-1;

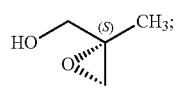

(vi) filtering the admixture obtained from step (v) to provide a filtrate comprising INT-1;
(vii) optionally treating the filtrate obtained from step (vi) with trimethylphosphite to quench unreacted cumene hydroperoxide ("the quenched filtrate"); and
(viii) treating the filtrate from step (vi) or the optionally quenched filtrate of step (vii) with triethylamine ($Et_3N$), 4-dimethylaminopyridine (DMAP), and 4-bromobenzene-1-sulfonyl chloride (BrsCl) to provide a second reaction mixture; and
(ix) allowing the contents of the second reaction mixture to react to provide an admixture comprising Compound 1.

2. The process of claim 1, wherein the molecular sieves used in step (i) of the water scavenger process is 4 Å molecular sieves.

3. The process of claim 1, wherein the solvent/diluent used in step (i) of the water scavenger process is methylene chloride or toluene.

4. The process of claim 1, wherein the solvent/diluent used in step (i) of the water scavenger process is methylene chloride or toluene.

5. The process of claim 1, further comprising:
(x) isolating Compound 1 from the admixture of step (ix).

6. A process for making Compound 1

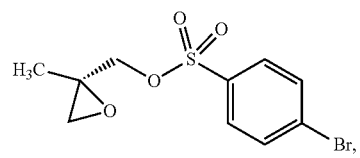

the process comprising:
(i) carrying out an azeotropic distillation of solution comprising cumene hydroperoxide and a solvent capable of forming an azeotrope to provide a first anhydrous solution;
(ii) cooling the first anhydrous solution;
(iii) carrying out an azeotropic distillation of a solution comprising methylallyl alcohol, (+)-di-isopropyl L-tartrate (L-DIPT), and a solvent capable of forming an azeotrope to provide a second anhydrous solution;
(iv) cooling the second anhydrous solution;
(v) adding titanium tetraisoproxide ($Ti(O-iPr)_4$) to the cooled second anhydrous solution in step (iv);
(vi) combining the cooled first solution from step (ii) with the cooled second anhydrous solution from step (v) to provide a first reaction solution;
(vii) allowing the contents of the first reaction solution from step (vi) to react to provide a solution comprising INT-1;
(viii) optionally treating the solution obtained from step (vii) with trimethylphosphite to quench unreacted cumene hydroperoxide; and
(ix) treating the solution obtained from step (vii), or the optionally quenched solution of step (viii), with triethylamine ($Et_3N$), 4-dimethylaminopyridine (DMAP), and 4-bromobenzene-1-sulfonyl chloride (BrsCl) to provide a reaction solution comprising Compound 1.

7. The process of claim 6, wherein the solvent capable of forming an azeotrope used in step (i) and step (iii) is methylene chloride or toluene.

8. The process of claim 6, further comprising:
(x) isolating Compound 1 from the reaction solution of step (ix).

9. A process for making the compound of formula I

wherein R¹ is chloro, bromo, or iodo,
the process comprising reacting Compound 1 of formula:
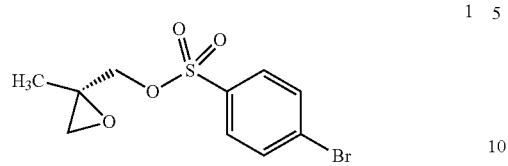
with a tetraethylammonium halide of formula $(CH_3CH_2)_4 N^+X^-$ in a suitable diluent/solvent,
wherein X is chloro, bromo, or iodo.
10. The process of claim 9, wherein X is iodo and the product is Compound 2
11. The process of claim 9, wherein the suitable diluent/solvent is dimethylformamide.
* * * * *